United States Patent [19]
Li et al.

[11] Patent Number: 5,312,747
[45] Date of Patent: May 17, 1994

[54] ISOLATION, PURIFICATION AND UTILIZATION OF SIALIDASE-L IN THE SYNTHESIS OF 2,7-ANHYDRO-N-ACETYLNEURAMINIC ACID AND FOR THE SELECTIVE CLEAVAGE OF SIALYL$\alpha$2-3 D-GALACTOSE LINKAGE

[76] Inventors: Yu-Teh Li; Su-Chen Li, both of 1717 Old Metairie St., Metairie, La. 70001

[21] Appl. No.: 15,413

[22] Filed: Feb. 8, 1993

Related U.S. Application Data

[63] Continuation-in-part of Ser. No. 628,912, Dec. 17, 1990.

[51] Int. Cl.$^5$ .......................... C12N 9/20; C12N 9/26
[52] U.S. Cl. .................................. 435/200; 435/201; 435/815
[58] Field of Search .................... 435/200, 201, 815

[56] References Cited

U.S. PATENT DOCUMENTS

| | | | |
|---|---|---|---|
| 4,071,408 | 1/1978 | Flashner et al. | 435/200 |
| 4,710,470 | 12/1987 | Uwajima et al. | 435/200 |
| 5,116,952 | 5/1992 | Sugimori et al. | 435/200 |

OTHER PUBLICATIONS

Schroder, et al., "Improved Methods For The Isolation And Structural Analysis Of Trace Amounts Of New Sialic Acids–Identification of N–Glycolyneuraminic Acid in In Man", *Glycoconjugates* Proceedings of the 7th Intl. Symp. on Glyconjugates, Ling-Ronneby, Jul. 17–23, 1983.
Li, et al., "A Novel Sialidase Which Releases 2,7-Anhydro-$\alpha$-N-acetylneuraminic Acid from Sialoglycoconjugates", *J. Biological Chemistry* 265: 21629–21633 (1990).
Gross, et al., "Identification of the internal acetal 5–acetamido-2,7-anhydro-3,5-dideoxy-D-*glycero*-D-*galacto*-nonulopyranose", *Carbohydrate Research* 41:344–350 (1975).
Lasky, Laurence "Selectins: Interpreters of Cell-Specific Carbohydrate Information During Inflammation", *Science* 258: 964–969 (1992).
Lifely and Cottee, "Formation And Identification Of Two Novel Anhydro Compounds Obtained By Methanolysis of N-Acetylneuraminic Acid And Carboxyl-Reduced, Meningococcal B Polysaccharide", *Carbohydrate Research* 107: 187–197 (1982).
Manzi, et al., "Identification of Substituted Sialic Acids by Fast-Atom Bombardment of their DMB–derivatives", *Glycobiology* 2: 459 (1992), Abstract 1.09 p. 459, Abstracts from the 21st Meeting of the Society for Complex Carbohydrates.
Suzuki, et al., "Characterization of 2,7-Anhydro-N-Acetylneuraminic Acid In Human Wet Cerumen", *J. Biochem.* 97: 509–515 (1985).
Schenkman, et al., "A Novel Cell Surface Tarns-Sialidase of Trypanosoma cruzi Generates a Stage-Specific Epitope Required for Invasion of Mammalian Cells", *Cell* 65: 1117–1125 (1991).
Schauer, Roland, "Analysis of Sialic Acids" *Methods in Enzymology* 138: 132–161 (1987).
Schauer, Roland, "Chemistry, Metabolism, and Biological Functions of Sialic Acids", *Advances in Carbohydrates Chemistry and Biochemistry* 40: 131–234 (1982).

*Primary Examiner*—Herbert J. Lilling
*Attorney, Agent, or Firm*—Albert P. Halluin

[57] ABSTRACT

The instant invention relates to the isolation, purification and utilization of sialidase-L, a novel enzyme capable of producing 2,7-anhydro N-acetylneuraminic acid by the selective cleavage of sialic acid-$\alpha 2 \rightarrow 3$D-galactose glycosidic bonds. The instant invention also relates to a method for the preparation of 2,7-anhydro-N-acetylneuraminic acid using sialidase-L. The instant invention also relates to methods for selectively cleaving sialic acid-$\alpha 2 \rightarrow 3$D-galactose glycosidic linkages and providing a means to selectively destroy the selectin ligands for the treatment of selectin-mediated inflammation. The instant invention also relates to methods for using 2,7-anhydro-N-acetylneuraminic acid and sialidase-L for the selective sialylation of acceptor glycosides to form sialic acid-$\alpha 2 \rightarrow 3$D-galactose glycosidic linkages.

4 Claims, 11 Drawing Sheets

N-ACETYLNEURAMINIC ACID

FIG. 1A-1

2,7-ANHYDRO-N-ACETYLNEURAMINIC ACID

2,7-ANHYDRO-N-ACETYLNEURAMINIC ACID

FIG. 1B-1

N-ACETYLNEURAMINIC ACID

ISOLATION, PURIFICATION AND UTILIZATION OF SIALIDASE-L IN THE SYNTHESIS OF 2,7-ANHYDRO-N-ACETYLNEURAMINIC ACID AND FOR THE SELECTIVE CLEAVAGE OF SIALYLα2-3 D-GALACTOSE LINKAGE

FUNDING

This invention was made with government support under grants awarded by the National Science Foundation and the National Institutes of Health.

RELATED APPLICATION

This application is a continuation-in-part of U.S. Ser. No. 07/628,912 filed Dec. 17, 1990.

TECHNICAL FIELD

This invention relates to the isolation, purification and utilization of sialidase-L. Sialidase-L has been found to selectively cleave sialic acid-α2→3D-galactose glycosidic linkages wherein 2,7-anhydro-N-acetylneuraminic acid is the cleavage product.

BACKGROUND OF THE INVENTION

Figure 1A:
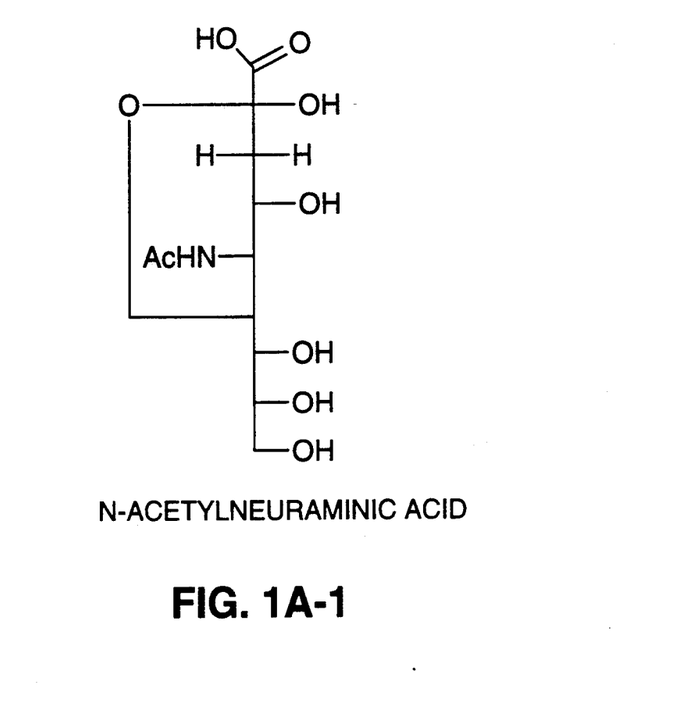
Figure 1A:
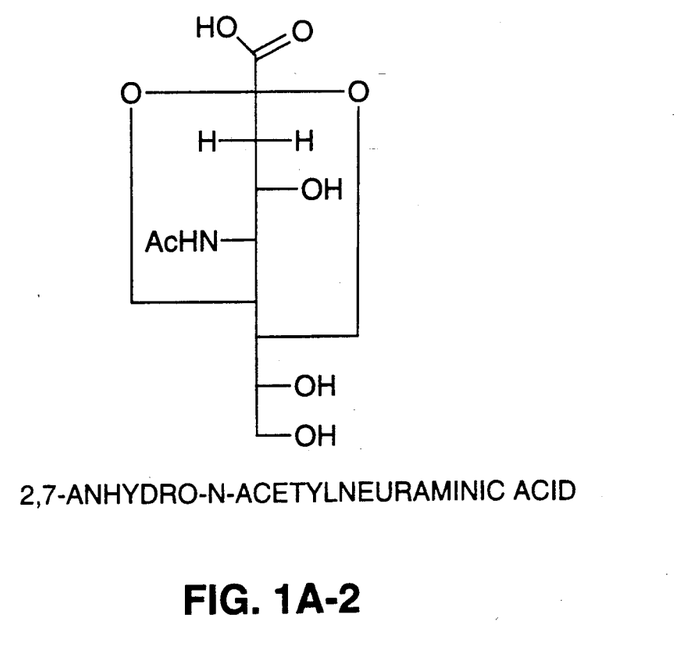
Figure 1B:
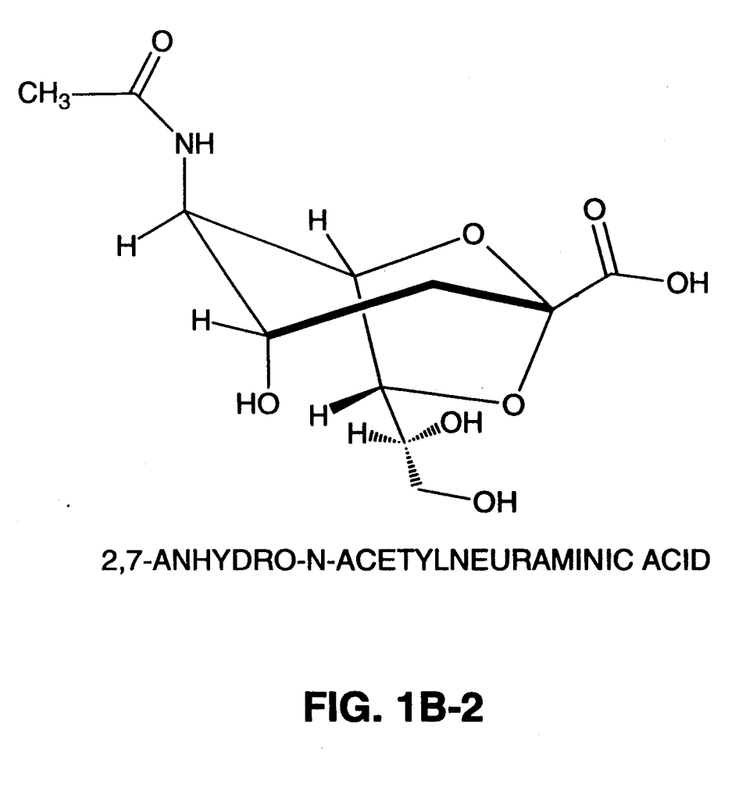
Figure 1B:
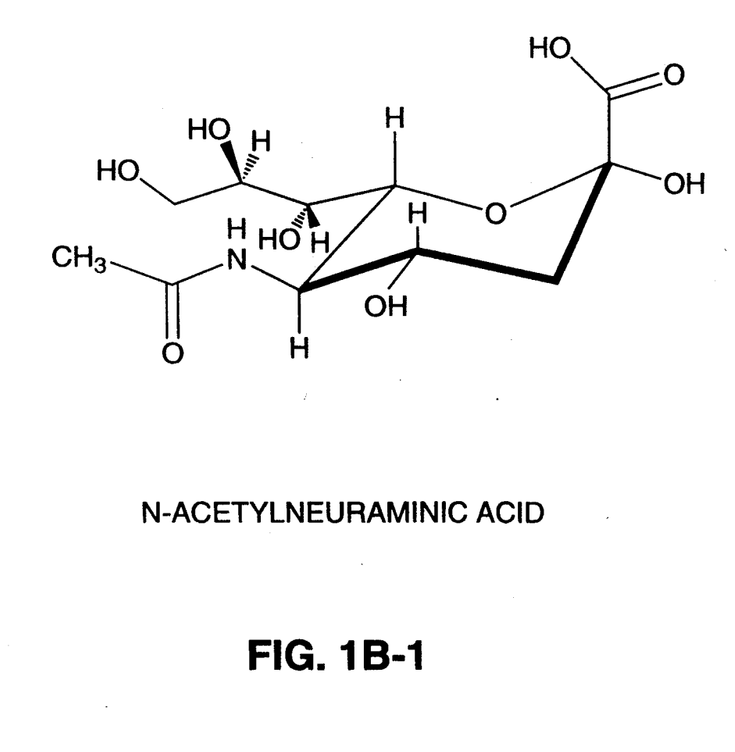

Sialic acids are acyl derivatives of neuraminic acid. N-Acetylneuraminic acid [FIG. 1] is one of the most frequently found sialic acids. (Blix, G., Gottschalk, A., and Klenk, E. (1959) Nature 179:1088). Sialic acids have been the subject of a great deal of research because they play several important and intriguing biological roles. For example, sialic acids play a role in cell biology by their negative charge, by influencing the conformation of glycoproteins, by acting as receptors for microorganisms, toxins and hormones and by masking receptors and recognition sites of molecules and cells. (Schauer, R. (1987) "Analysis of Sialic Acids" Methods in Enzymology 138:132-161).

Figure 2:
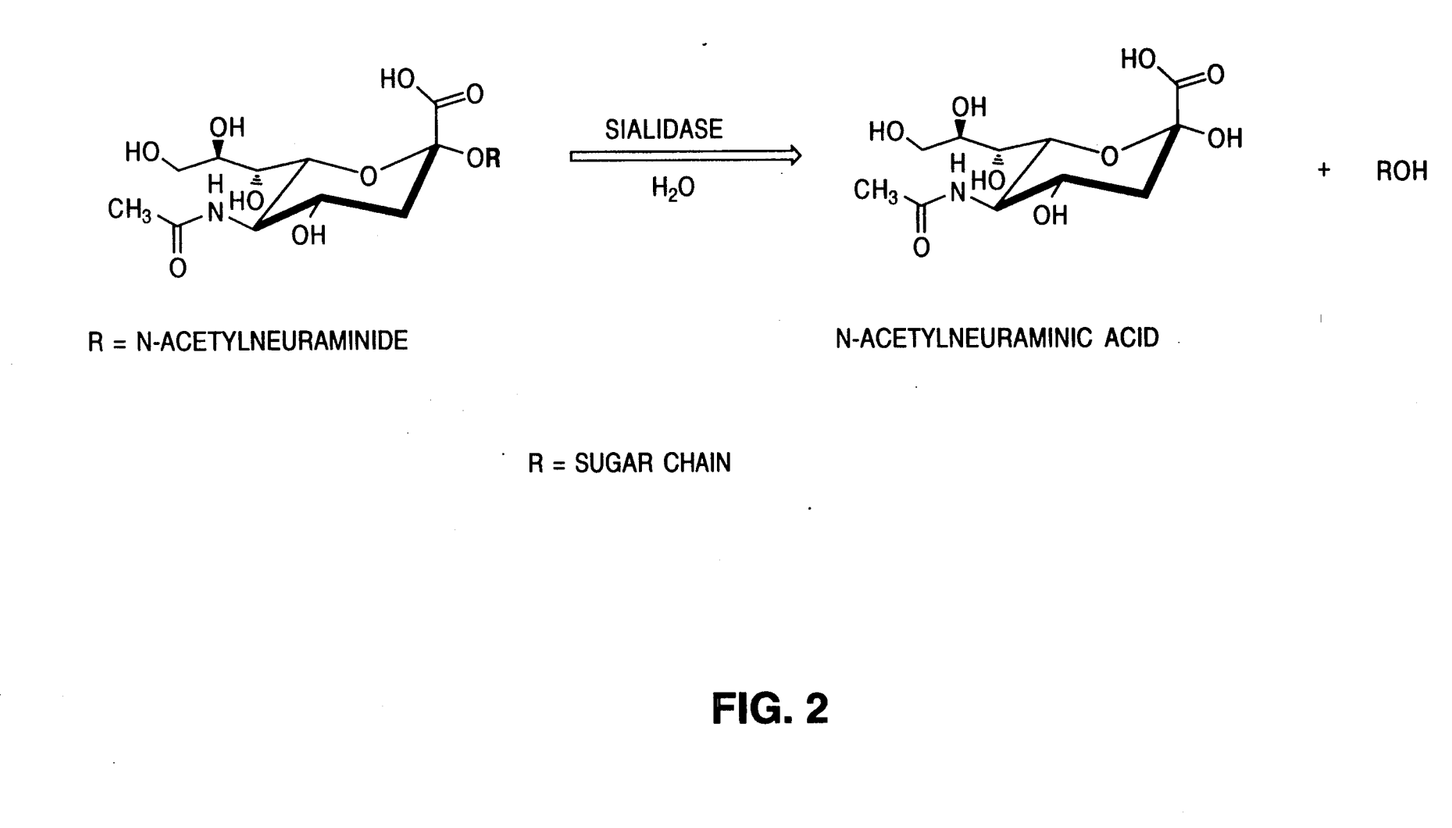

Through research on sialic acids, a large number of sialidases have been isolated. In general, sialidases are a class of enzymes capable of cleaving the glycosidic linkage of sialic acid. [FIG. 2]. To date, all sialidases that have been isolated release free sialic acid as the enzymatic product. (Schauer, R. (1982) "Chemistry, Metabolism and Biological Functions of Sialic Acids" Advances in Carbohydrate Chemistry and Biochemistry 40:131-234).

2,7-Anhydro-N-acetylneuraminic acid, a relative of sialic acid, has also been isolated. [FIG. 1]. Gross, S. K, et al., (1975) Carbohydrate Res. 41:344-350, reported detection of 5-acetimido-2,7-anhydro-3, 5-dideoxy-D-glycero-D-galacto-nonulopyranose in the acid hydrolysate of glycosidically-linked sialic acid in which the carboxylic function had been reduced to an alcohol. Lifely, M. R., et al., ((1982) Carbohydrate Res. 107:187-197), showed that methanolysis of sialic acid gave the methyl ester of 2,7-anhydro-N-acetylneuraminic acid in addition to the methyl ester ketoside of sialic acid. The presence of 2,7-anhydro-N-acetylneuraminic acid in rat urine was reported by Schroder, et al. (1983) "Proc 7th Int. Symp. Glycoconjugates", Chester, Mass., eds., Rahms, Lund, Sweden, pp. 162-163. 2,7-Anhydro-N-acetyneuraminic acid has also been detected in human wet cerumen (ear wax) by Suzuki, M., et al., (1985) J. Biochem (Tokyo) 97:509-515.

The presence of 2,7-anhydro-N-acetylneuraminic acid in human wet cerumen (ear wax) suggests that this unusual sialic acid derivative may have bactericidal activity. Since 2,7-anhydro-N-acetylneuraminic acid is resistant to degradation by sialyl-aldolase, this compound can also serve as a reservoir for sialic acids in the biological system. The biological function of 2,7-anhydro-N-acetylneuraminic acid is still largely unknown. This is due to the lack of an effective synthetic method for its production.

The close relationship of 2,7-anhydro-N-acetylneuraminic acid to sialic acid, both having a stereochemically identical carbon backbone, is evident when one compares the Fischer diagram representations of N-acetylneuraminic acid and 2,7-anhydro-N-acetylneuraminic acid. [See FIG. 1(a)]. However, 2,7-anhydro-N-acetylneuraminic acid has a three-dimensional structure that is distinct from sialic acid. [FIG. 1(b)]- Of significance is the bicyclic ring structure of 2,7-anhydro-N-acetylneuraminic acid. Unlike sialic acid which is in a $^2C_5$ conformation with all of its pyranose ring substituents equatorial except the substituents at the anomeric carbon (C-2), 2,7-anhydro-N-acetylneuraminic acid is in a $^5C_2$ conformation with all of the pyranose ring substituents axial. Furthermore, N-acetylneuraminic acid is a reducing sugar while 2,7-anhydroneuraminic acid is non-reducing. Thus, despite the similarity of sialic acid and 2,7-anhydro-N-acetylneuraminic acid based on their Fischer representations, the three-dimensional structures and chemical properties of these two compounds are quite distinct. Hence, sialic acid and 2,7-anhydro-N-acetylneuraminic acid are structurally distinct and dissimilar compounds.

Figure 3:
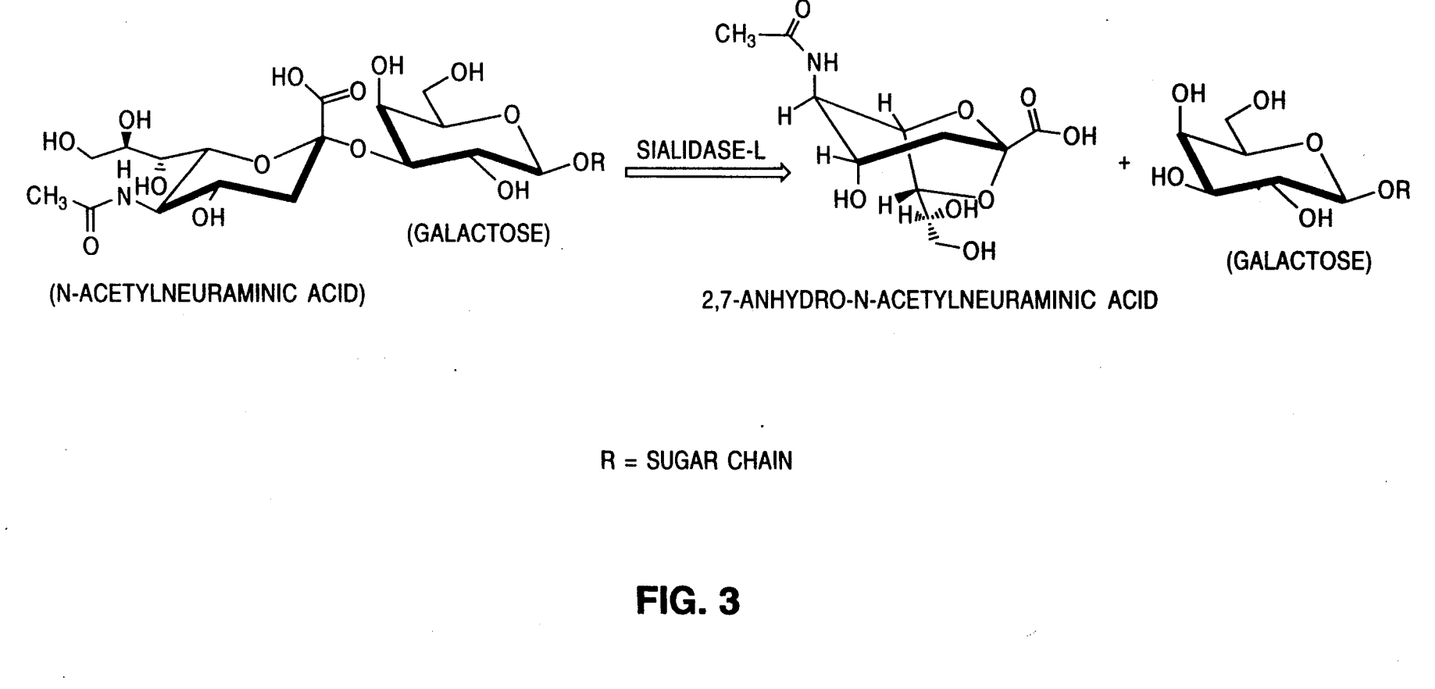
FIG. 3 shows the enzymatic reaction for sialidase-L.

Recently, Y. T. Li reported the presence of an enzyme, named "Sialidase-L", in a leech that exhibits novel specificity and produces 2,7-anhydro-N-acetylneuraminic acid as the unexpected cleavage product. In addition to the synthetic substrate, 4-methylumbelliferyl-N-acetylneuraminic acid, sialidase-L was reported to selectively cleave sialic acid linked α2→3 to D-galactose from substrates including fetuin, α1-acid glycoprotein, neuraminlactose, and whale nasal keratan sulfate to yield 2,7-anhydro-N-acetylneuraminic acid as the sole observed product. [FIG. 3]. Sialidase-L does not cleave sialic acids that are linked α2→6 to D-galactose, α2→6 to N-acetyl-D-galactosamine or sialic acid linked α2→8 or α2→9 to N-acetylneuraminic acid. Furthermore, sialidase-L does not convert free sialic acid to 2,7-anhydro-N-acetylneuraminic acid. See Abstract for the 21st annual meeting of the Society for Complex Carbohydrates, Nashville, Tenn., Nov. 11-14, 1992, Glycobiology, volume 2, p. 459, 1992.

No specific information regarding the procedure for the isolation and properties of sialidase-L were disclosed at the meeting of the Society for Complex Carbohydrates. Isolation of sialidase-L has significant utility since it enables the development of methodology for producing 2,7-anhydro-neuraminic acid. Furthermore, sialidase-L enables selective cleavage of sialic acid-α2→3D-galactose glycosidic linkages in sialoglycoconjugates.

SUMMARY OF THE INVENTION

The instant invention relates to the enzyme sialidase-L in purified and isolated form. A further embodiment of the instant invention relates to the enzyme sialidase-L possessing at least 200 units of activity per mg protein.

The instant invention also relates to a method of purifying sialidase-L from M. decora consisting of the steps of preparation of a concentrated crude enzyme preparation and sequential chromatography of the crude enzyme preparation using columns packed with Fractogel TSK DEAE-650(M), octyl CL-4B, Fractogel EMD SO$_3$-650(M), Sephadex G-100, Matrex Blue A and Hypatite C.

The instant invention also relates to a method for preparing 2,7-anhydro-N-acetylneuraminic from sialoglycoconjugates using sialidase-L.

The instant invention also relates to a method for using sialidase-L to selectively cleave sialic acid-α2→3D-galactose linkages in sialoglycoconjugates.

The instant invention also relates to the use of sialidase-L for the selective destruction of sialic acid-α2→3D-galactose linkage in selectin ligands to treat the selectin-mediated inflammation.

The instant invention also relates to the use of 2,7-anhydro-N-acetylneuraminic acid as the substrate and sialidase-L to form sialyl -α2→3D-galactose linkages in suitable acceptor glycosides.

Further objectives and advantages other than those set forth above will become apparent from the detailed description of the invention and the accompanying drawings.

BRIEF DESCRIPTION OF DRAWINGS

FIG. 1A-1 and FIG. 1A-2 compares the structure of FIG. 1A-1, N-acetylneuraminic acid and FIG. 1A-2, 2,7-anhydro-N-acetylneuraminic acid as depicted in a Fischer diagram.

FIG. 1B-1 and FIG. 1B-2 compares the structures of FIG. 1B-1, N-acetylneuraminic acid and FIG. 1B-2, 2,7-anhydro-N-acetylneuraminic acid as depicted in its three-dimensional configuration.

Table 1 shows the results of the stepwise purification of sialidase-L.

Table 2 shows the structures of GM3, GM2, GM1a, GM1b and GQ1b.

Scheme 1 summarizes the extraction of sialidase-L from leeches.

Scheme 2 summarizes the sequential chromatographic purification of sialidase-L from the leech extract.

DETAILED DESCRIPTION OF THE INVENTION

The instant invention relates to the isolation, purification and utilization of sialidase-L, a novel enzyme capable of producing 2,7-anhydro-N-acetylneuraminic acid by the selective cleavage of sialic acid-α2→3D-galactose glycosidic bonds. The instant invention also relates to a method for the preparation of 2,7-anhydro-N-acetylneuraminic acid using sialidase-L. The instant invention also relates to methods for selectively cleaving sialic acid-α2→3D-galactose glycosidic linkages. Since many selectin ligands contain sialic acid-α2→3D-galactose linkage, sialidase-L can be used for the selective destruction of sialic acid-α2→3D-galactose in the selectin ligands to treat selectin-mediated inflammation. The instant invention also relates to methods for the use of 2,7-anhydro-N-acetylneuraminic acid and sialidase-L for the selective sialylation of acceptor glycosides to form sialic acid-α2→3D-galactose glycosidic linkages.

1) Purification of Sialidase-L From the Leech

Fluorometric assay of N-acetylneuraminic acid-cleaving activity using 4-methylumbelliferyl-N-acetylneuraminic acid as the substrate is used to follow the purification of sialidase-L. (See Potier, M., et al., *Anal. Biochem.* (1979) 94:287-296). The assay mixture contains the following components: 4-methylumbelliferyl-N-acetylneuraminic acid, 20 nmol; sodium acetate buffer, pH 5.5, 5 μmol; and an appropriate amount of enzyme. 100 μl of assay mixture is used for each assay. After the mixture is incubated at 37° C. for a predetermined period of time, the reaction is terminated by the addition of 1.5 ml of 0.2M sodium acetate buffer, pH 9.8 to the assay mixture. The concentration of free 4-methylumbelliferone is determined by a spectrofluorometer. One unit of activity (4-methylumbelliferyl-N-acetylneuraminic acid-cleaving activity) is defined as the amount of enzymic activity necessary to liberate 1 nmol of 4-methylumbelliferone per minute at 37° C.

The procedure for extraction and purification of sialidase-L from the leech are summarized in Schemes 1 and 2.

Unless otherwise indicated, the isolation of sialidase-L is carried out at a temperature between 0° and 5° C. Centrifugation is routinely carried out at 10,000×g for 30 minutes using a refrigerated centrifuge. For extracting sialidase-L, leeches are ground with a meat grinder and homogenized with 3 volumes of cold distilled water containing 1 mM EDTA in a Waring blender at 30 seconds intervals for a total of 2 minutes. The homogenate is then centrifuged to obtain a crude extract. While stirring, the pH of this crude extract is brought to 4.8 by the dropwise addition of saturated citric acid solution. The precipitate formed is removed by centrifugation and the pH of the clear supernatant is quickly adjusted to 6.5 by the dropwise addition of a saturated Na$_2$HPO$_4$ solution. Protamine sulfate (2 g/100 ml of H$_2$O) is then added dropwise to the supernatant until the precipitate ceases to appear. The precipitate is removed by centrifugation and the supernatant is concentrated by a Millipore Minitan ultrafiltration unit to obtain a concentrated crude enzyme preparation.

Figure 4:
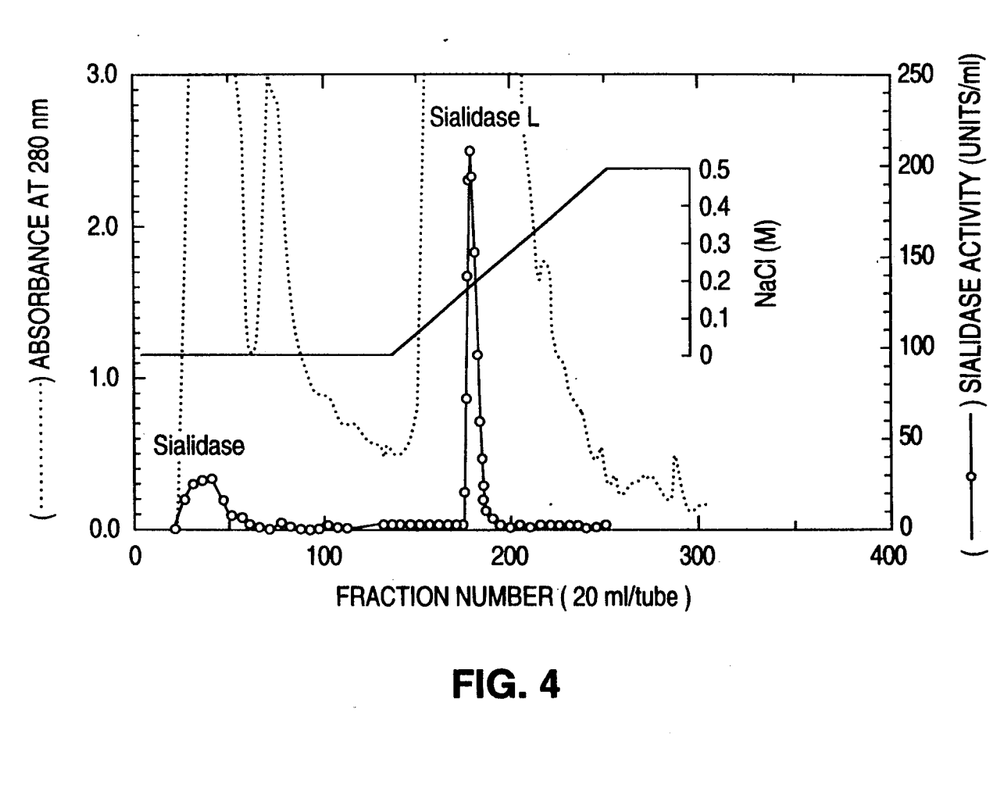
FIG. 4 shows the elution pattern for the purification of sialidase-L using Fractogel TSK DEAE-650(M) Chromatography.
Figure 5:
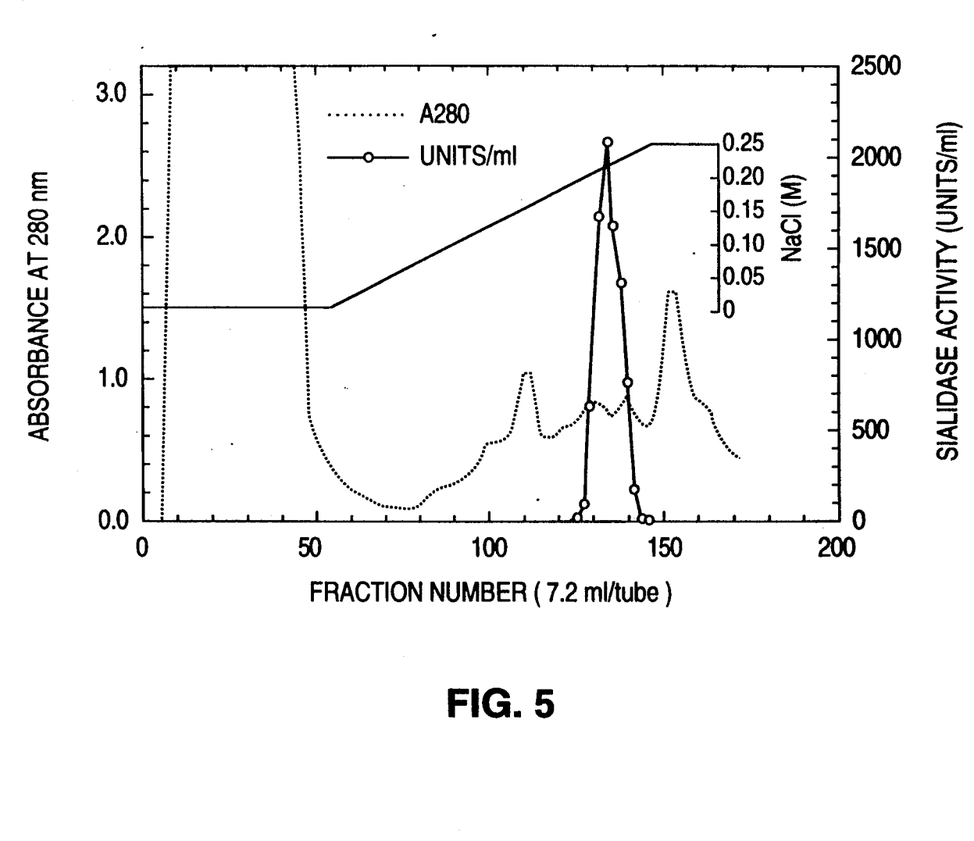
FIG. 5 shows the elution pattern for the purification of sialidase-L using Fractogel SO$_3$-propyl Chromatography.
Figure 6:
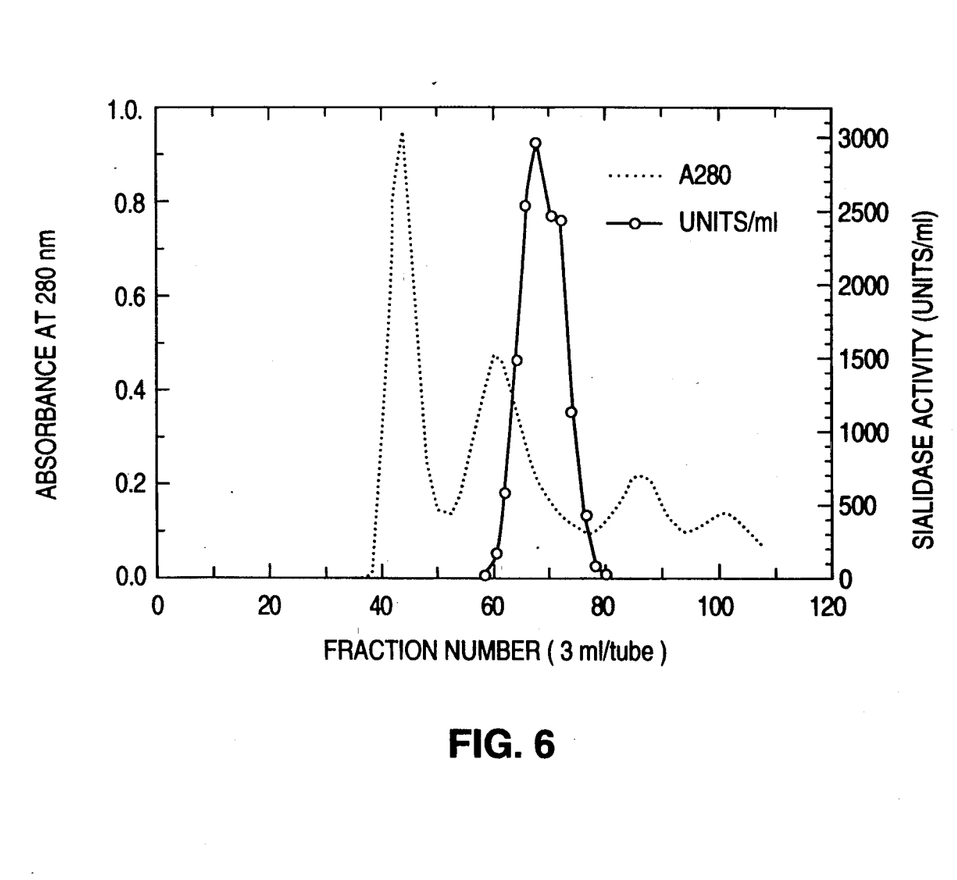
FIG. 6 shows the elution pattern for the purification of sialidase-L using Sephadex G-100 Chromatography.
Figure 7:
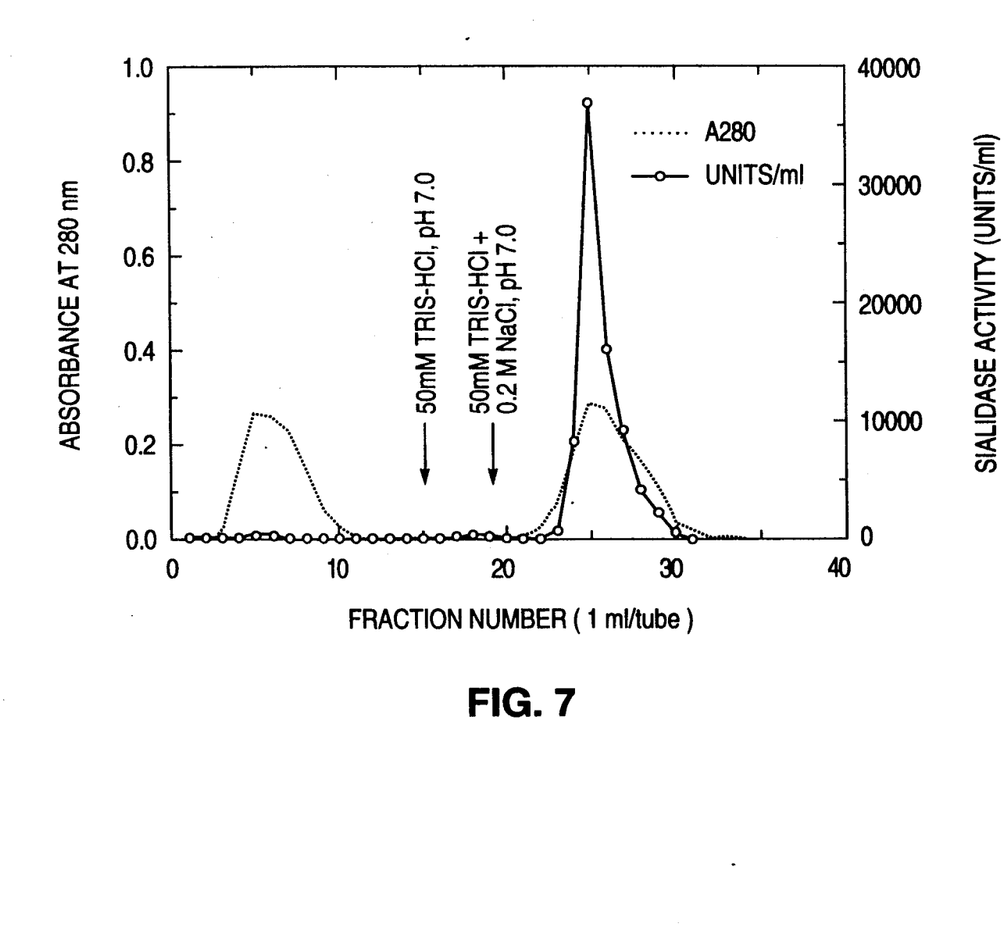
FIG. 7 shows the elution pattern for the purification of sialidase-L using Matrex Blue A Chromatography.
Figure 8:
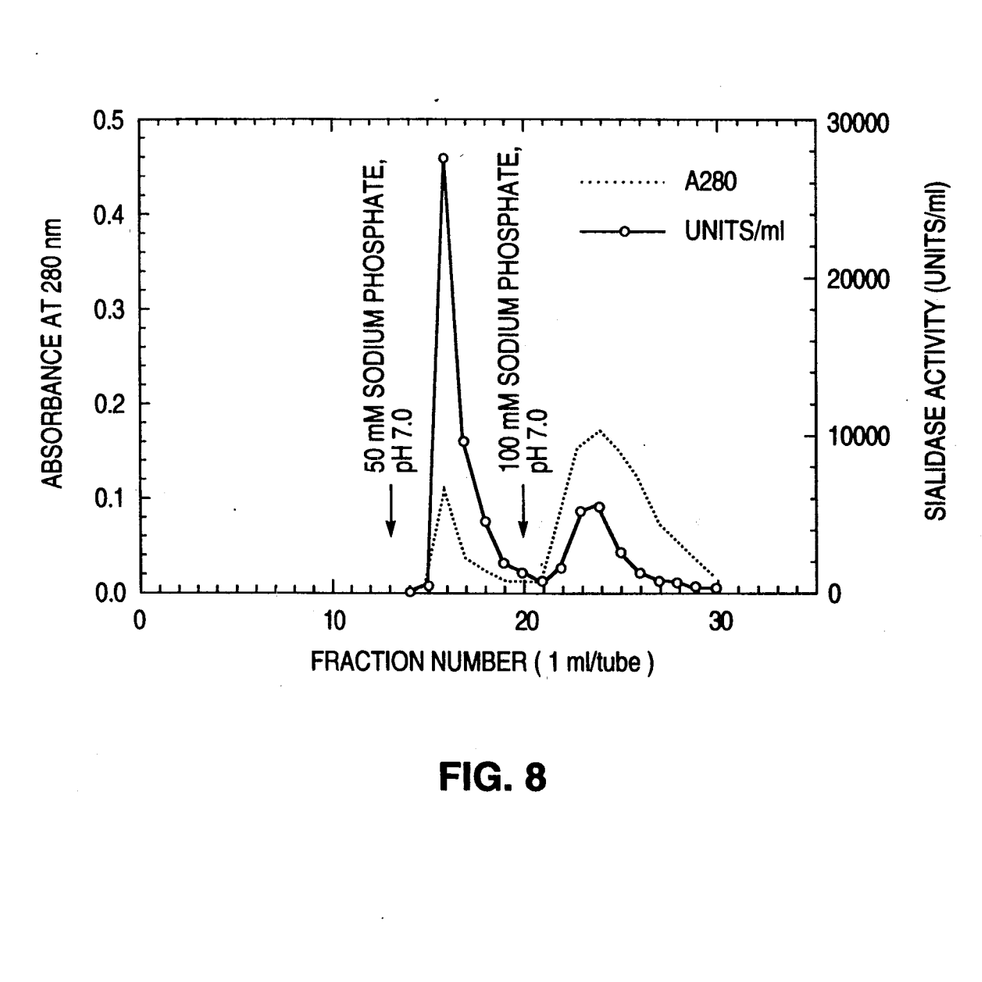
FIG. 8 shows the elution pattern for the purification of sialidase-L using Hypatite C Chromatography.

This crude enzyme preparation is then purified by sequential column chromatography as shown in Scheme 2. FIGS. 4-8 depict the sequential chromatographic purification of sialidase-L using Fractogel TSK DEAE-650(M) Chromatography [FIG. 4], Fractogel SO3-propyl Chromatography [FIG. 5], Sephadex G-100 Chromatography [FIG. 6], Matrex Blue A Chromatography [FIG. 7] and Hypatite C Chromatography [FIG. 8] respectively. Sialidase-L is clearly separated and purified from the regular sialidase as shown in FIG. 4. Table 1 summarizes the purification and recovery of sialidase-L from 20 kg of leech using sequential column chromatography as depicted in Scheme 2.

TABLE 1

Purification of sialidase-L from 20 Kg of leech

| Procedures | Total activity units ×1000 | Total protein mg | Specific activity units/mg ×1000 | Recovery % | Purification fold |
|---|---|---|---|---|---|
| Fractogel DEAE | 180 | 9,365.00 | 0.02 | 100 | 1 |
| Octyl Sepharose | 150 | 4,325.00 | 0.04 | 83 | 2 |
| Fractogel SP | 124 | 43.36 | 2.86 | 69 | 143 |
| Sephadex G100 | 79 | 4.64 | 17.03 | 44 | 852 |
| Matrex Blue A | 52 | 1.57 | 33.12 | 29 | 1,656 |
| Hypatite C | 28 | 0.13 | 215.00 | 15 | 10,750 |

1 unit = 1 nmole of 4-methylumbelliferone released per minute at 37° C.

Figure 9:
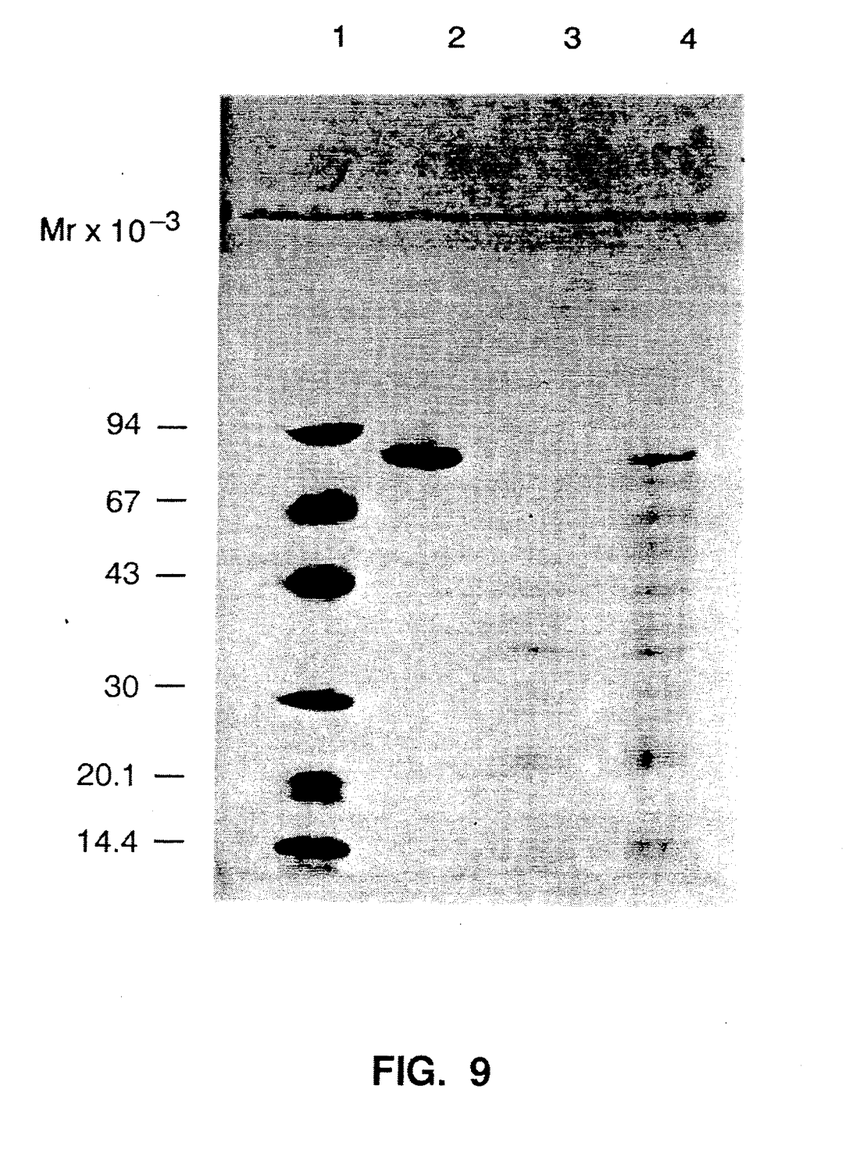
FIG. 9 shows the sodium dodecylsulfate-polyacrylamide gel electrophoresis of purified sialidase-L.

Using the procedures described above, sialidase-L is purified over 10,000 fold with a 15% recovery. (Table 1). As shown in FIG. 9, the final preparation gives one single protein band corresponding to the molecular weight of 84,000 when analyzed by sodium dodecyl sulfate polyacrylamide gel electrophoreses. The optimal pH of the enzyme is between pH 5.5 and 6.0. The highly purified sialidase-L is very unstable in 50 mM sodium acetate buffer, pH 5.5. However, the enzyme is stable for at least three months when stored at $-35°$ C. in the presence of 10% glycerol. The electrophoretically homogeneous sialidase-L is free from protease activity and other glycosidase activities such as the regular sialidase, $\alpha$- and $\beta$- galactosidases, $\alpha$- and $\beta$-mannosidases and $\alpha$- and $\beta$-fucosidases, $\alpha$-N-acetylgalactosaminidase, $\beta$-N-acetylhexosaminidase and ceramideglycanase. For practical purposes the enzyme after Matrex blue A chromatography is pure enough to be used as an enzyme reagent for the synthesis of 2,7-anhydro-N-acetylneuraminic acid and for the selective cleavage of $\alpha 2$-3 D-galactose linked sialic acids from sialoglycoconjugates.

2) Synthesis of 2,7-Anhydro-N-Acetylneuraminic Acid Using Sialidase-L

4-Methylumbelliferyl-N-acetylneuraminic acid (commercially available), 100 mg is incubated with 150 units of sialidase-L in 25 ml of 50 mM sodium acetate buffer, pH 5.5 at 37° C. for 17 hours. The reaction is terminated by the addition of an equal volume of ethanol and the precipitate is removed by centrifugation. The clear supernatant is evaporated to dryness, dissolved in 30 ml of chloroform/methanol (2:1 v/v) and subjected to Folch partitioning (Folch, J. Lees, M. and Sloan Stanley, G. H. (1957) J. Biol. Chem. 226, 479–509), by vortexing with 6 ml of water. The 2,7-anhydro-N-acetylneuraminic acid is recovered in the aqueous phase. The organic phase is washed with 8 ml of water. The aqueous phase and the water wash are combined and evaporated to dryness, dissolved in 8 ml of water and applied to a Bio-Gel p-6 column (2.5×90 cm) equilibrated with water. The column is eluted with water at 20 ml per hour wherein 5-ml fractions are collected. Three microliter aliquots of each fraction are analyzed by thin-layer chromatography (solvent:n-butanol/acetic acid/water (2:1:1 v/v) and resorcinol spray to locate the product). Fractions containing 2,7-anhydro-N-acetylneuraminic acid are pooled, lyophilized, dissolved in 20 ml of water and applied to a Dowex-1×8 column (formate form, 2×50 cm) equilibrated with water. After washing the column with 800 ml of water to remove the unadsorbed material, the column is eluted with 500 ml of 0.2M formic acid followed by 400 ml of 0.4M formic acid at a flow rate of 40 ml per hour; 10-ml fractions are collected. Under this condition 2,7-anhydro-N-acetylneuraminic acid is eluted by 0.4M formic acid and the eluate is evaporated to dryness to obtain 15 mg of pure 2,7-anhydro-N-acetylneuraminic acid. The above scheme can be proportionally scaled up for large scale preparation of 2,7-anhydro-N-acetylneuraminic acid.

By fast atom bombardment mass spectroscopy, the molecular weight of 2-,7-anhydro-N-acetylneuraminic acid is 291 which is equivalent to the molecular weight of N-acetylneuraminic acid (309) minus one molecule of water (18). Unlike N-acetylneuraminic acid, 2-7-anhydro-N-acetylneuraminic acid does not give color with periodate/thiobarbituric acid reaction (Warren, L., J. Biol. Chem. 234, 1971–1975, 1959). It is also refractory to N-acetylneuraminic acid aldolase and reduction with sodium borohydride. The overall structure of 2,7-anhydro-N-acetylneuraminic acid has been determined by mass spectrometry and NMR-spectroscopy (Li, et al., (1990) J. Biol. Chem. 265, 21629–21633).

3) Selective Cleavage of Sialic Acid-$\alpha 2 \rightarrow 3$D-Galactose Linkage From Sialollycoconjugates Sialic acids can be linked to complex carbohydrate chains through $\alpha 2 \rightarrow 3$D-galactose, $\alpha 2 \rightarrow 6$D-galactose, $\alpha 2 \rightarrow 6$D-N-acetylgalactosamine, $\alpha 2 \rightarrow 8$N-acetylneuraminic acid and $\alpha 2 \rightarrow 9$N-acetylneuraminic acid linkages. Among these linkages, only $\alpha 2 \rightarrow 3$D-galactose linkage is susceptible to sialidase-L. Therefore, it is advantageous to use sialidase-L to selectively cleave $\alpha 2 \rightarrow 3$D-galactose linkage without destroying other sialosyl linkages. Since biologically active sialoglycoconjugates are often available in small quantities, we have devised the following micromethod for detecting/destroying sialic acid-$\alpha 2 \rightarrow 3$D-galactose linkages in sialoglycoconjugates.

Figure 10:
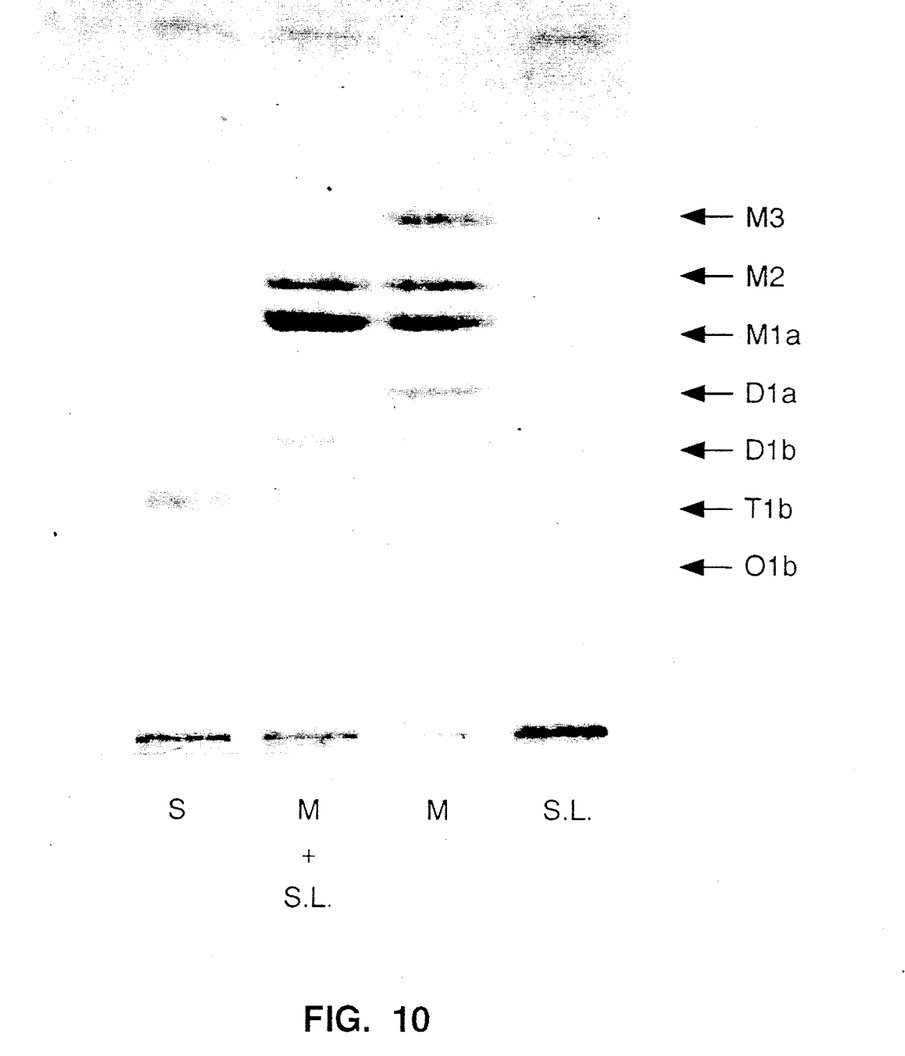
FIG. 10 shows the results from incubating a ganglioside mixture with sialidase-L.

Sialoglycoconjugate, 10 nmole in 15 $\mu$l 50 mM sodium acetate buffer, pH 5.5 is placed in a 3×30 mm microconical tube and incubated with 0.2 unit of sialidase-L (in 5 $\mu$l 50 mM sodium acetate buffer, pH 5.5) at 37° C. for 15 hours. After incubation, 5 $\mu$l of the reaction mixture is directly analyzed by thin-layer chromatography using chloroform/methanol/0.2% CaCl$_2$(55:40:9, v/v) as the developing solvent. Sialoglycoconjugates on the thin-layer plate are identified by resorcinol spray. FIG. 10 shows the results of the incubation of a ganglioside mixture which contains GM3, GM2, GM1a, GD1a, GD1b, GT1b and GQ1b with sialidase-L. As shown in this figure, sialidase-L selectively destroyed GM3, GD1a and GT1b with concomitant production of 2,7-anhydro-N-acetylneuraminic acid. The increase in GM1a and GD1b after incubation indicates the conversion of GD1a to GM1a and GT1b to GD1b by sialidase-L. Table 2 shows the structures of GM3, GM2, GM1a, GD1b, GT1b and GQ1b.

TABLE 2
Structures of GM3, GM2, GM1a, GD1a, GD1b, GT1b and GQ1b

Note:
Gal = galactose, Glc = glucose, GalNac = N-acetylgalactosamine, NeuAc = N-acetylneuraminic acid, Cer = ceramide. The internal NeuAc in GM2 and GM1a is resistant to sialidases.

4) Treatment of Selectin-Mediated Inflammation

A family of glycoproteins called selectins have the characteristic ability of being able to use certain carbohydrate structures in an adhesion mechanism to promote the localization of leukocytes to a region of inflammation. It has been shown that many selectin ligands have sialyl-Lewis$^x$ (N-acetylneuraminic acid-$\alpha2\rightarrow3$ D-galactose-[L-fucose-$\alpha1\rightarrow3$]-N-acetyl-D-glucosamine) epitope or sialyl-Lewis$^a$ (N-acetylneuraminic acid-$\alpha2\rightarrow3$ D-galactose $\beta1\rightarrow3$ [L-fucose$\alpha1\rightarrow4$]-N-acetyl-D-glucosamine) epitope. See Lasky, L. A. (1992) "Selectins: Interpreters of Cell Specific Carbohydrate Information During Inflammation" *Science* 258:964.969. Selective cleavage of the N-acetylneuraminic acid-$\alpha2\rightarrow3$ D-galactose linkage in selectin ligands by sialidase-L can be used to treat the selectin-mediated inflammation.

5) Selective Enzymatic Synthesis of Sialyl-$\alpha2\rightarrow3$Galactose Linkage Using 2,7-Anhydro-N-Acetylneuraminic Acid as the Substrate In addition to being able to selectively cleave sialic acid linked $\alpha2\rightarrow3$ to galactose, sialidase-L can be used to selectively form a sialic acid-$\alpha2\rightarrow3$D-galactose linkage using 2,7-anhydro-N-acetylneuraminic acid as the substrate. By driving the equilibrium in reverse through the addition of excess 2,7-anhydro-N-acetylneuraminic acid, sialidase-L can be used to selectively form $\alpha2\rightarrow3$ sialyl - galactose linkages in suitable acceptor glycosides including desialylated forms of keratan sulfate, $\alpha1$ acid glycoprotein, fetuin, neuramin-lactose, GM3 and GD1a. See Schenkman, S., et al., (1991) "A novel cell surface trans-sialidase of *Trypanosoma cruzi* generates a stage specific epitope required for invasion of mammalian cells." *Cell* 65:1117–1125.

While the invention of this patent application is disclosed by reference to the details of preferred embodiments, it is to be understood that this disclosure is intended in an illustrative rather than limiting sense, as it is contemplated that modifications will readily occur to those skilled in the art, within the spirit of the invention and the scope of the appended claims.

What is claimed is:

1. The enzyme sialidase-L in purified and isolated form wherein the purified enzyme has a molecular weight of 84,000 daltons when analyzed by sodium dodecyl sulfate polyacrylamide gel electrophoreses and an optimal pH of between pH 5.5 and 6.0, the purified enzyme being unstable in 50 mM sodium acetate buffer at pH 5.5 and stable for at least three months when stored at −35° C. in the presence of 10% glycerol and where the enzyme is capable of synthesizing 2,7-anhydro-N-acetylneuraminic acid.

2. The enzyme sialidase-L of claim 1 wherein the enzyme possesses at least 200 units of activity per mg protein.

3. A method of purifying sialidase-L from *M. decora* consisting of the steps of preparation of a concentrated crude enzyme preparation and sequential chromatography of the crude enzyme preparation using columns packed with Fractogel TSK DEAE-650(M), octyl CL-4b, Fractogel EMD SO$_3$-650(M), Sephadex G-100, Matrex Blue A and Hypatite C, and recovering the purified sialidase-L enzyme, wherein the purified enzyme has a molecular weight of 84,000 daltons when analyzed by sodium dodecyl sulfate polyacrylamide gel electrophoreses and an optimal pH of between pH 5.5 and 6.0, the purified enzyme being unstable in 50 mM sodium acetate buffer at pH 5.5 and stable for at least three months when stored at −35° C. in the presence of 10% glycerol and where the enzyme is capable of synthesizing 2,7-anhydro-N-acetylneuraminic acid.

4. The enzyme of claim 2 wherein enzyme is purified from *M. decora* consisting of the steps of preparation of a concentrated crude enzyme preparation; and sequential chromatography of the concentrated crude enzyme preparation using columns packed with Fractogel TSK DEAE-650(M), octyl CL-4b, Fractogel EMD SO$_3$-650(M), Sephadex G-100, Matrex Blue A and Hypatite C.

* * * * *